United States Patent
Ide (10) Patent No.: US 11,382,497 B2
(45) Date of Patent: Jul. 12, 2022

(54) BENDING OPERATION WIRE ATTACHING STRUCTURE AND ENDOSCOPE

(71) Applicant: Olympus Corporation, Hachioji (JP)

(72) Inventor: Yuka Ide, Cambridge, MA (US)

(73) Assignee: OLYMPUS CORPORATION, Tokyo (JP)

( * ) Notice: Subject to any disclaimer, the term of this patent is extended or adjusted under 35 U.S.C. 154(b) by 597 days.

(21) Appl. No.: 16/269,789

(22) Filed: Feb. 7, 2019

(65) Prior Publication Data

US 2019/0167070 A1    Jun. 6, 2019

Related U.S. Application Data

(63) Continuation of application No. PCT/JP2017/015455, filed on Apr. 17, 2017.

(30) Foreign Application Priority Data

Aug. 10, 2016    (JP) .............................. JP2016-157710

(51) Int. Cl.
*A61B 1/008* (2006.01)
*A61B 1/00* (2006.01)
(Continued)

(52) U.S. Cl.
CPC ................ *A61B 1/008* (2013.01); *A61B 1/00* (2013.01); *A61B 1/0055* (2013.01);
(Continued)

(58) Field of Classification Search
CPC ... A61B 1/00147; A61B 1/0055; A61B 1/008; A61B 1/0057
See application file for complete search history.

(56) References Cited

U.S. PATENT DOCUMENTS 5,174,277 A * 12/1992 Matsumaru .......... A61B 1/0055
                                                                600/142
6,482,149 B1 * 11/2002 Torii .................... A61B 1/0055
                                                                600/141
(Continued)

FOREIGN PATENT DOCUMENTS

JP       05-020701       3/1993
JP       05-020705       3/1993
(Continued)

OTHER PUBLICATIONS

International Search Report and Written Opinion from corresponding International Application No. PCT/JP2017/015455, dated Jun. 27, 2017.
(Continued)

*Primary Examiner* — Aaron B Fairchild
(74) *Attorney, Agent, or Firm* — Oliff PLC (57) ABSTRACT

The disclosed technology is directed to a bendable tube bendable by a bending wire that comprises a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion having a first insertion region and a second insertion region. The bending wire is inserted from within the distal-end bending piece outwardly of the distal-end bending piece through the first insertion region. The bending wire is inserted from outside the distal-end bending piece into the distal-end bending piece through the second insertion region. The bending wire disposed outside the distal-end bending piece between the first insertion region and the second insertion region being attached to the distal-end bending piece by the attaching portion.

9 Claims, 9 Drawing Sheets

(51) Int. Cl.
  *A61B 1/05* (2006.01)
  *A61B 1/005* (2006.01)
  *A61B 1/06* (2006.01)
  *G02B 23/24* (2006.01)

(52) U.S. Cl.
  CPC ........ *A61B 1/0057* (2013.01); *A61B 1/00101* (2013.01); *A61B 1/00147* (2013.01); *A61B 1/05* (2013.01); *A61B 1/0676* (2013.01); *G02B 23/2476* (2013.01)

(56) References Cited

U.S. PATENT DOCUMENTS

| | | | | |
|---|---|---|---|---|
| 2009/0326325 | A1* | 12/2009 | Naito | A61B 34/70 600/141 |
| 2010/0004508 | A1* | 1/2010 | Naito | A61B 1/00133 600/141 |
| 2013/0041223 | A1* | 2/2013 | Kato | A61B 1/0051 600/121 |

FOREIGN PATENT DOCUMENTS

| | | |
|---|---|---|
| JP | 05-285089 | 11/1993 |
| JP | 10-258025 | 9/1998 |
| JP | 2000-275546 | 10/2000 |
| JP | 2001-037705 | 2/2001 |
| JP | 2001-231742 | 8/2001 |
| JP | 2006-006451 | 1/2006 |
| JP | 3780056 | 3/2006 |
| JP | 2013-034787 | 2/2013 |

OTHER PUBLICATIONS

Japanese Office Action No. JP2017-553207, dated Oct. 31, 2017.
Japanese Office Action JP2017-553207, dated Feb. 8, 2018.

* cited by examiner

BENDING OPERATION WIRE ATTACHING STRUCTURE AND ENDOSCOPE

CROSS-REFERENCE TO RELATED APPLICATIONS

This application is a continuation application of PCT Application No. PCT/JP2017/015455 filed on Apr. 17, 2017, which in turn claim priority to the Japanese Patent Application No. 2016-157710 filed on Aug. 10, 2016 in Japan which is hereby incorporated by reference in its entirety.

TECHNICAL FIELD

The technology disclosed herein relates to a bendable tube structure, a bending operation wire attaching structure, and an endoscope. The bendable tube structure is disposed in a bendable part. The bending operation wire attaching structure is formed by disposing the bendable tube structure in the bendable part.

DESCRIPTION OF THE RELATED ART

In recent years, endoscopes that are inserted into a body of an examinee have been widely used in the medical field and the industrial field. In particular, an endoscope used in the medical field is capable of observing an organ in a body cavity of an examinee by inserting a tubular insertion portion of the endoscope into the body cavity or, if necessary, treating such an organ with a treating instrument inserted through a treating instrument insertion channel in the endoscope. Conventional endoscope inserts incorporate a known arrangement having a bendable part that can easily be inserted into an examinee.

A bendable part of an endoscope includes a plurality of bending operation wires for performing the bending function of the endoscope. The user of the endoscope can bend the bendable part by pulling or loosening the bending operation wires. These bending operation wires are as many and/or long as the directions in which the bendable part is to bend. These bending operation wires are attached to a distal-end part of the endoscope. For example, Japanese Patent Laid-Open No. 1998-258025 discloses a technology for attaching a plurality of bending operation wires to a distal-end part of an endoscope.

According to the structure by which the bending operation wires are connected, the bending operation wires are attached to the distal end of a joint piece by attaching members. The joint piece is used as a bending piece. The attached members are compressed and secured to the distal ends of the bending operation wires. Therefore, the bending operation wires and the insertion portion are attached to each other with a sufficient degree of attachment strength that is guaranteed regardless of the material of the bending operation wires. However, the structure by which the multiple bending operation wires are connected is problematic in that it (i) involves a process of compressing the attaching members to the distal-end part of the endoscope and (ii) requires an arrangement for placing the bending operation wires along the outer periphery of the bending piece on the distal end, resulting in a corresponding increase in the profile and diameter of the bendable part.

One aspect of the disclosed technology is directed to a bendable tube bendable by a bending operation wire that comprises a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion having a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region. The bending operation wire is attached to the distal-end bending piece by the attaching portion.

BRIEF SUMMARY OF EMBODIMENTS

One aspect of the disclosed technology is directed to a bendable tube bendable by a bending operation wire that comprises a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion having a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region being attached to the distal-end bending piece by the attaching portion.

Another aspect of the disclosed technology is directed to an endoscope comprises a bendable tube bendable by a bending operation wire having a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion includes a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region. The bending operation wire is attached to the distal-end bending piece by the attaching portion. An insertion portion includes the bendable tube. The insertion portion is formed as a slender tube. A manipulator joined to the insertion portion for manipulating the bendable tube. The bending operation wire is folded back and disposed in the distal-end bending piece.

Another aspect of the disclosed technology is directed to an endoscope comprises a bendable tube bendable by a bending operation wire having a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion includes a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region being attached to the distal-end bending piece by the attaching portion. An insertion portion includes the bendable tube. The insertion portion is formed as a slender tube. A manipulator joined to the insertion portion for manipulating the bendable tube. The bending operation wire is folded back and disposed in the distal-end bending piece.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 9 is a cross-sectional view of a distal-end bending piece with bending operation wires attached thereto that are compatible with directions which a bendable part is bendable in.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It also should be noted with respect to the description hereinafter that the figures based on the embodiments of the disclosure are schematic in nature and the relationship between the thicknesses and widths of various components, the ratios of the thicknesses of the various components, etc. are different from those in reality, and the relationship between dimensions and the ratios thereof may be different between the figures.

The technology disclosed herein solve the problems noted in the prior art. The technology disclosed herein provides a bending operation wire attaching structure and an endoscope in which bending operation wires for bending a bendable part are attached in place in a simplified fashion and the diameter of a bendable part is prevented from increasing accordingly.

A bending operation wire attaching structure according to an aspect of the present disclosure includes a bendable tube, a distal-end bending piece, a bending operation wire, and an attaching portion. The bendable tube is disposed in a bendable part of an insertion portion and made up of a plurality of bending pieces. The distal-end bending piece is disposed at the foremost end of the bendable tube and includes a flat portion. The bending operation wire is attached to the distal-end bending piece for bending the bendable part. The attaching portion is disposed in the flat portion and includes two insertion regions. The bending operation wire is inserted from within the distal-end bending piece outwardly of the distal-end bending piece through the two insertion regions. The bending operation wire is folded back and attached in position on the flat portion by the attaching portion.

An endoscope according to an aspect of the present disclosure has a bending operation wire attaching structure including a bendable tube, a distal-end bending piece, a bending operation wire, and an attaching portion. The bendable tube is disposed in a bendable part of an insertion portion and made up of a plurality of bending pieces. The distal-end bending piece is disposed at the foremost end of the bendable tube and includes a flat portion. The bending operation wire is attached to the distal-end bending piece for bending the bendable part. The attaching portion is disposed in the flat portion and includes two insertion regions. The bending operation wire is inserted from within the distal-end bending piece outwardly of the distal-end bending piece through the insertion regions. The bending operation wire is folded back and is attached in position on the flat portion by the attaching portion. The bending operation wire attaching structure is incorporated in the bendable part.

Figure 1:
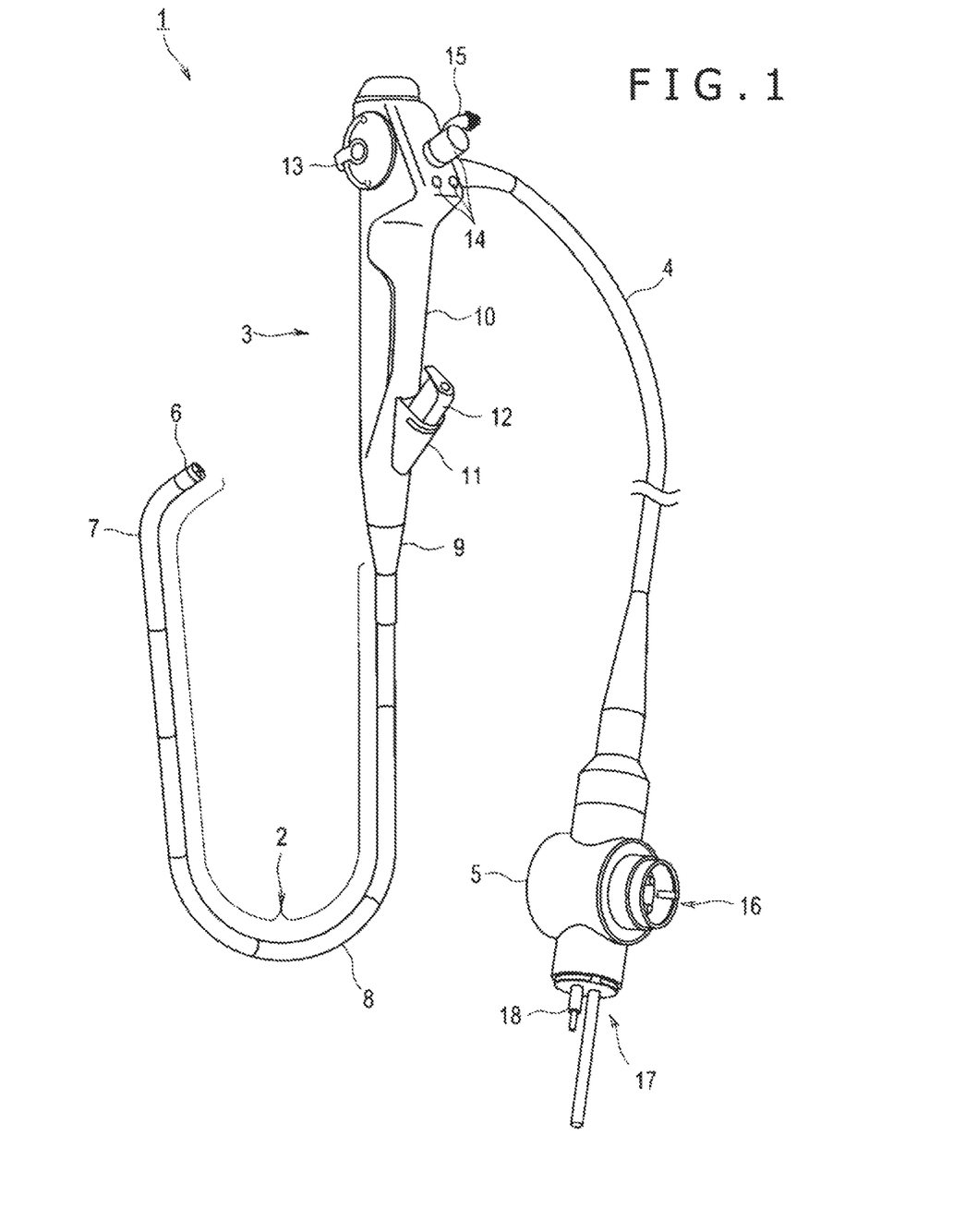
FIG. 1 is a perspective view depicting an arrangement of an endoscope according to an aspect of the technology disclosed herein.

As depicted in FIG. 1, an electronic endoscope (hereinafter referred to simply as "endoscope") 1 according to the present embodiment mainly includes an insertion portion 2, a manipulator 3, a universal cord 4, and an endoscope connector 5. The insertion portion 2 is formed tubular in shape. The manipulator 3 is joined to the proximal end of the insertion portion 2. The universal cord 4 is used as an endoscope cable extending from the manipulator 3. The endoscope connector 5 is disposed on the distal end of the universal cord 4. The insertion portion 2 is a flexible tubular member having a distal-end part 6, a bendable part 7, and a flexible tubular part 8. The bendable part is used as an endoscopic bendable part according to the present embodiment. The distal-end part 6 contains therein an image capturing unit illuminating means, not depicted, etc. The image capturing unit is used as an image capturing device, not depicted, including image capturing means.

The endoscope 1 is not limited to an electronic endoscope, but may be a fiber scope in which an image guide fiber free of an image capturing unit is disposed in the insertion portion 2. The bendable part 7 incorporates therein a bendable tube structure to be described hereinafter. The bendable part 7 includes a mechanism that can positively be bent in two vertical directions (UPWARD and/or DOWNWARD) by turning a bending lever 13 to be described hereinafter among manipulating members of the manipulator 3. The bendable part 7 is not limited to the type described hereinbefore, but may be of a type that can be bent in four directions (fully circumferential directions about an axis by moving a bending lever in upward, downward, leftward, and rightward directions, UP-DOWN/RIGHT-LEFT) including leftward and rightward directions in addition to the upward and downward directions, or in an upward direction (UP direction) only.

The flexible tubular part 8 is a pliable tubular member that is passively flexible. A treating instrument insertion channel, various signal wires, a light guide, etc. are inserted in the flexible tubular part 8 and all of which are described hereinafter. The various signal wires extend from the image capturing unit contained in the distal-end part 6 and extend from the manipulator 3 into the universal cord 4. The light guide directs illuminating light from a light source device and emits the illuminating light from the distal-end part 6. The manipulator 3 includes a snap preventing portion 9, a grip 10, a biopsy port 11, and a suction valve 15. The snap preventing portion 9 is disposed on a distal end of the manipulator 3 and is connected to the flexible tubular part 8 in covering the proximal end of the flexible tubular part 8. The grip 10 is joined to the snap preventing portion 9 and is grippable by hand of the user when the user operates the endoscope 1. The manipulating means is disposed on outer surfaces of the grip 10 for performing various endoscopic functions.

The manipulating means of the manipulator 3 includes, for example, a bending lever 13 and a plurality of manipulating members 14. The bending lever 13 is for bending the bendable part 7. The plurality of manipulating members 14 is for carrying out a manipulating process for passing air and water or a manipulating process for performing suction, and manipulating processes for manipulating the image capturing means and the illuminating means. The biopsy port 11 is a that has a treating instrument insertion port through which any of various treating instruments, not depicted, can be inserted. The biopsy port 11 is held in fluid communication with the treating instrument insertion channel through a branch member in the manipulator 3.

A forceps plug 12 is disposed in the biopsy port 11. The forceps plug 12 is used as a lid for opening and closing the treating instrument insertion port and can be (replaceably) mounted in and removed from the biopsy port 11. The universal cord 4 is a compound cable. The various signal wires, a light guide, and an air and water delivery tube are inserted in the compound cable. The various signal wires extend from the distal-end part 6 of the insertion portion 2 through the insertion portion 2 to the manipulator 3 and then extend from the manipulator 3. The light guide extends from the light source device, not depicted. The air and water delivery tube extends from an air and water delivery device, not depicted.

The endoscope connector 5 includes an electric connector member 16, a light source connector 17, and an air and water delivery plug 18. The electric connector member 16 is located on a side surface of the endoscope connector 5. The electric connector member 16 is connected to a signal cable. The signal cable is connected to a video processor, not depicted, as an external device. The light source connector 17 is connected to a light guide bundle to be described hereinafter and an electric cable, not depicted. The light guide bundle and the electric cable are connected to the light source device as an external device. The air and water delivery plug 18 is connected to an air and water delivery tube, not depicted, extended from the air and water delivery device, not depicted, as an external device. An arrangement of a distal-end portion of the insertion portion 2 of the endoscope 1 according to the present embodiment will be described hereinafter.

Figure 2:
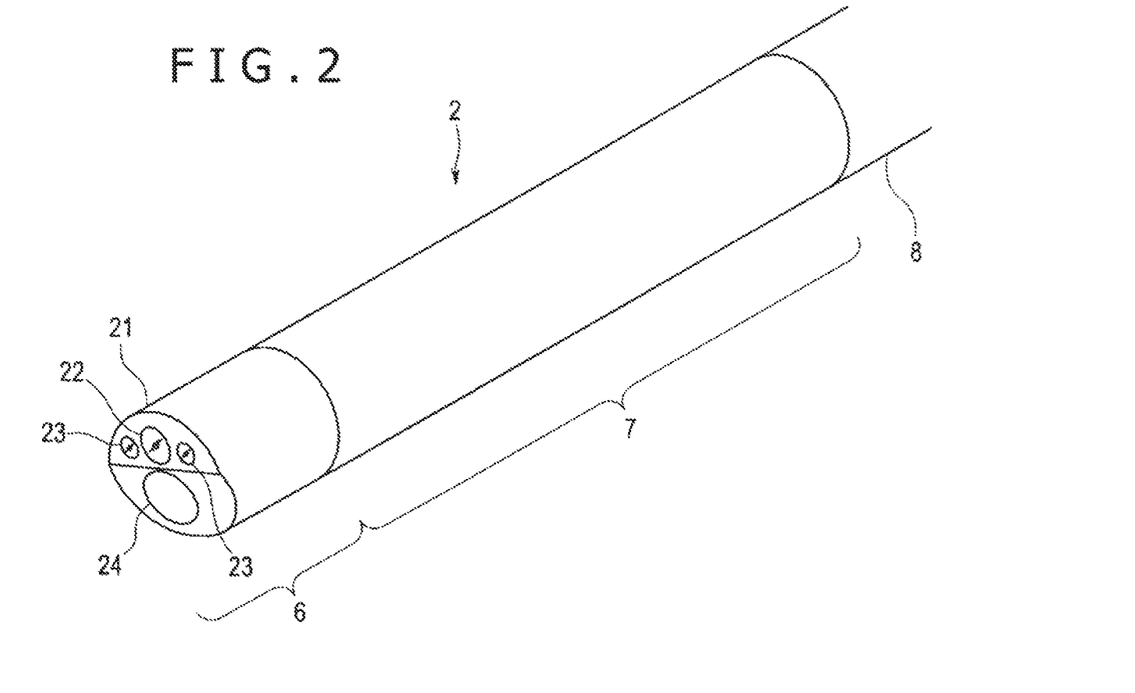
FIG. 2 is a perspective view depicting a distal-end part of an insertion portion.

The distal-end part 6 of the insertion portion 2 has a distal-end rigid part 21 (Depicted in FIG. 2) as a rigid frame substantially in the shape of a cylinder made of metal, resin, or the like. The distal-end rigid part 21 has an observation window 22, two illumination windows 23, and an opening 24 of the treating instrument insertion channel, defined in a distal-end face thereof. As seen best in FIG. 2, the bendable part 7 is covered with a sleeve of bendable rubber disposed over the outer circumference thereof. The bendable rubber is hermetically attached to respective ends of the distal-end part 6 and the flexible tubular part 8 by wrapping with thread and boding with adhesion on the thread. The bendable part 7 houses therein a bendable tube made up of a plurality of bending pieces, not depicted. The bendable tube housed in the bendable part 7 will be described hereinafter.

Figure 3:
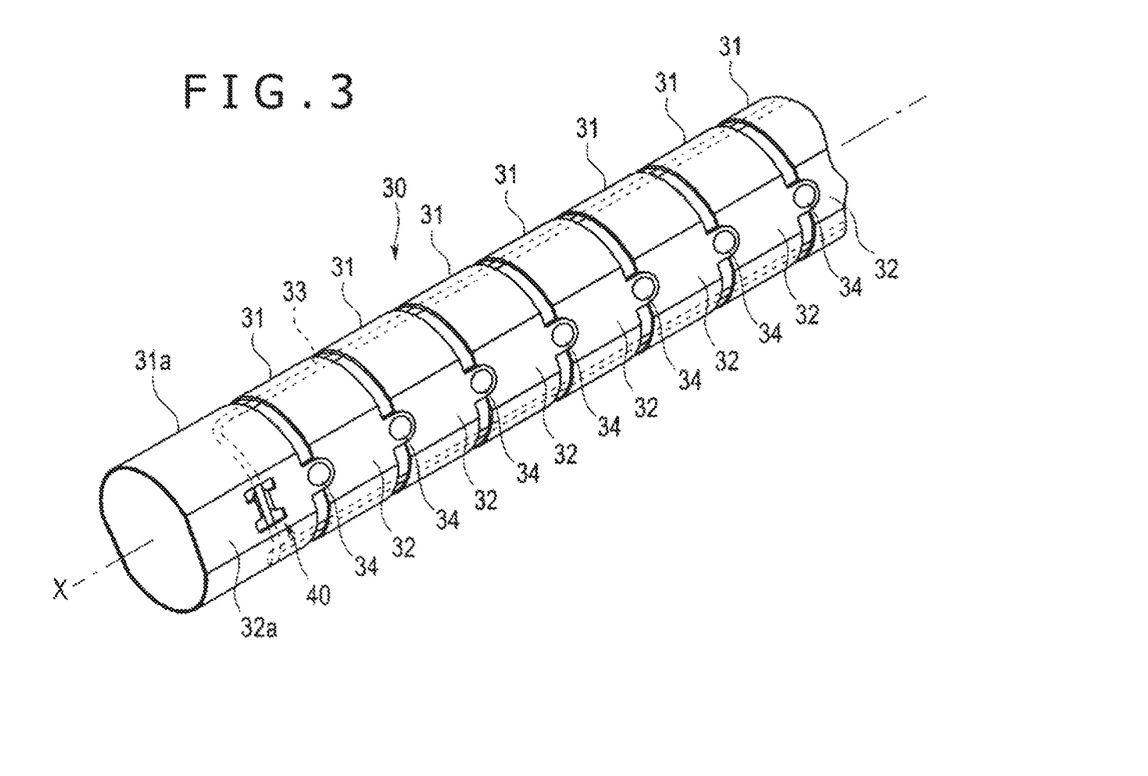
FIG. 3 is a perspective view of a bendable tube that is portion of the insertion portion depicted in FIG. 2.

As depicted in FIG. 3, the bendable tube 30, according to the present embodiment has a distal-end bending piece 31a and a bending piece group as defined hereinafter. The distal-end bending piece 31a is connected to the distal-end rigid part 21 and disposed at the foremost end of the bendable tube 30. The bending piece group is defined by a plurality of bending pieces 31 arranged successively rearwardly from the distal-end bending piece 31a at substantially equal intervals with predetermined spaces therebetween. The distal-end bending piece 31a and the bending pieces 31 are made of metal such as stainless steel or rigid resin in a substantially ring shape (annular shape). The distal-end bending piece 31a and the bending pieces 31 have flat portions 32a and 32 at both sides thereof, respectively. The flat portions 32a and 32 provide flat surfaces lying along the directions in which the bendable part 7 is bendable. In other words, the flat portions 32a and 32 provide flat surfaces substantially parallel to the trajectory followed by the bendable part 7 when it is bent.

The multiple bending pieces 31 each of which having string guides, not depicted. The string guides are wire receivers directed radially inwardly where a bending operation wire 33 is disposed. The string guides are disposed in point-symmetry positions about a central axis "X". Each bending piece 31 has two string guides spaced in vertical directions or upward/downward directions across the insertion portion 2. According to the present embodiment, the bendable part 7 is of a bidirectionally bendable structure that is bendable in two vertical directions (upward/downward). Needless to say, the bendable part 7 may be of a quad-directionally bendable structure that is bendable in upward, downward, leftward, and rightward directions (UD/RL). Each bending piece 31 is manufactured inexpensively as it is pressed to shape if made of metal and it is molded to shape if made of rigid resin. The multiple bending pieces 31 are juxtaposed along the central axis "X" with predetermined gaps therebetween, and are rotatably and movably coupled together by pivots or rivets 34 and/or other fasteners. Since the bendable tube 30 has been well known heretofore, other structural details thereof will not be described hereinafter. A bending operation wire attaching structure incorporated in the bendable tube 30 will be described hereinafter.

Figure 4:
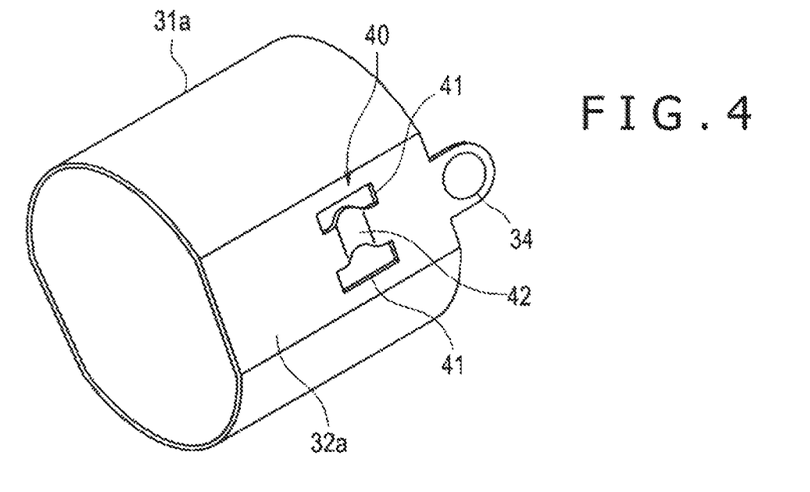
FIG. 4 is a perspective view of a distal-end bending piece that is a portion of the bendable tube depicted in FIG. 3.

As depicted in FIG. 4, the distal-end bending piece 31a of the bendable tube 30 according to the present embodiment includes an attaching portion 40. The attaching portion 40 is used as a wire locking portion by which the bending operation wire 33 is folded back and locked on one of the flat portions 32a. The attaching portion 40 includes two rectangular openings 41 defined in the distal-end bending piece 31a along the central axis "X" and a web 42 disposed between the two openings 41. The web 42 is recessed in the radially inward direction of the distal-end bending piece 31a.

Figure 5:
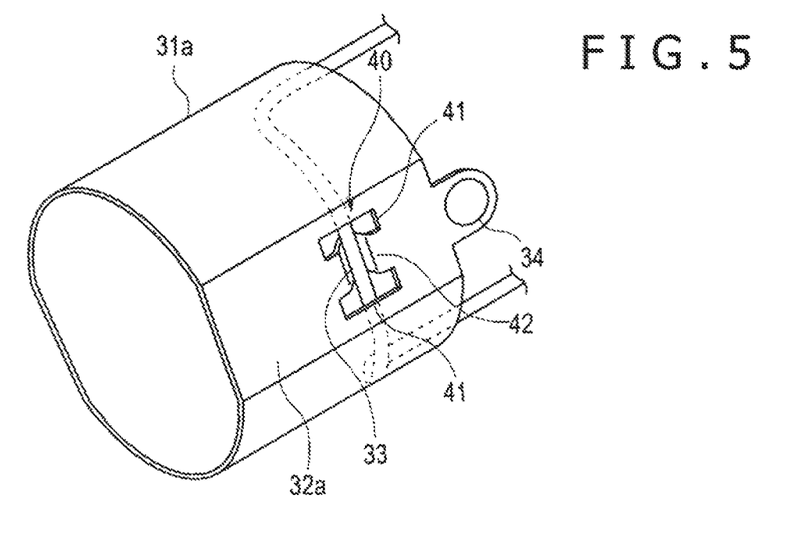
FIG. 5 is a perspective view of the distal-end bending piece with a bending operation wire attached thereto.

As depicted in FIG. 5, in the attaching portion 40, the single bending operation wire 33 extends from within the distal-end bending piece 31a outwardly of the distal-end bending piece 31a through one of the openings 41, then along an outer surface of the web 42, and then from outside the distal-end bending piece 31a through the other openings 41 into the distal-end bending piece 31a. The two openings 41 thus are used as wire insertion regions through which the bending operation wire 33 is inserted. The web 42 secures the bending operation wire 33 against movement. The bending operation wire 33 may be attached to the web 42 by solder, silver solder or adhesive. The bending operation wire 33 disposed on the web 42 is folded back and inserted through the two string guides, not depicted. The string guides are spaced in the vertical directions or up/down direction on the inside of each bending piece 31. The bending operation wire 33 extends rearwardly of the bendable tube 30. As described hereinbefore, the bendable tube 30 according to the present embodiment has two rearwardly extended bending operation wire 33 formed by (i) hooking the single bending operation wire 33 on the attaching portion 40 of the distal-end bending piece 31a, (ii) folding back the bending operation wire 33, and (iii) crimping the web 42 to secure the bending operation wire 33.

Figure 6:
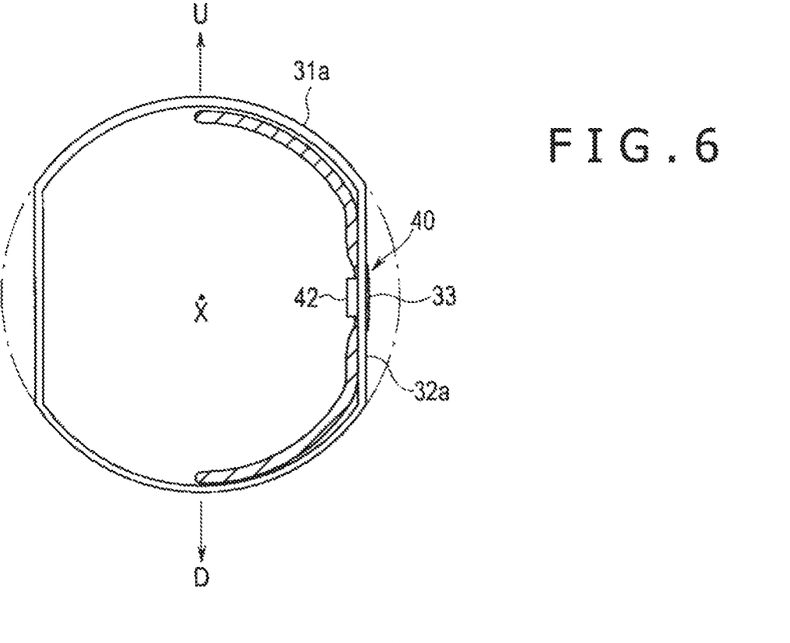
FIG. 6 is a front elevational view of the distal-end bending piece with the bending operation wire attached thereto.

As depicted in FIG. 6, the attaching portion 40 attaches the bending operation wire 33 and is formed on one of the flat portions 32a of the distal-end bending piece 31a. Therefore, the outside diameter of the bendable part 7 does not increase and hence is prevented from increasing even if the bending operation wire 33 projects outwardly from the flat portion 32a.

Figure 7:
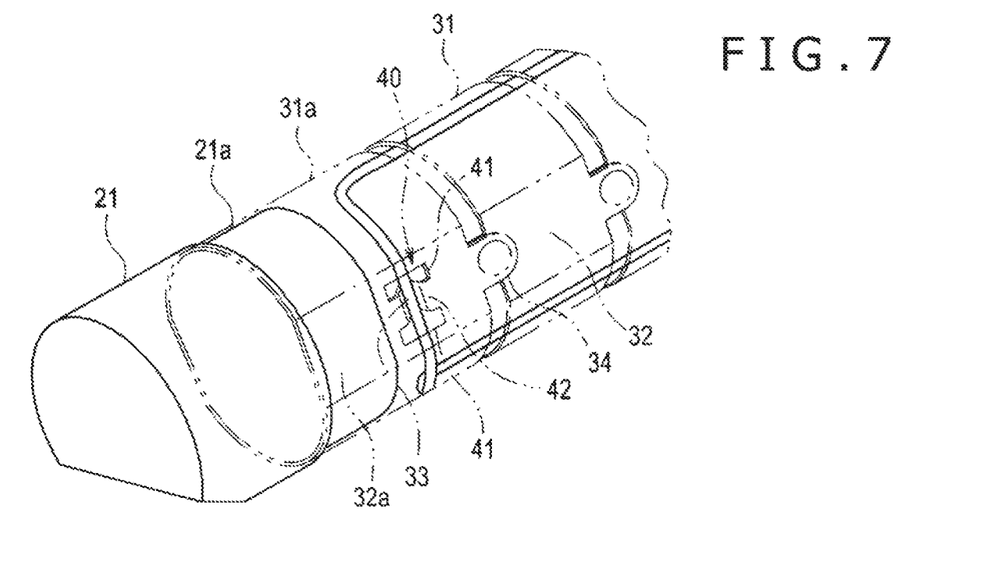
FIG. 7 is a perspective view depicting an example of a bendable tube with a distal-end rigid part fitted therein.

As depicted in FIG. 7, a reduced-diameter portion 21a is used as a fitting member on the proximal end of the distal-end rigid part 21. The reduced-diameter portion 21a is fitted in the distal-end bending piece 31a. The reduced-diameter portion 21a may, for example, not reach the attaching portion 40 on the distal-end bending piece 31a when the reduced-diameter portion 21a is fitted in the distal-end bending piece 31a. In this case, the bending operation wire 33 extends in the vertical directions (UD), free of the bending operation wire 33 on a proximal-end portion from the attaching portion 40.

Figure 8:
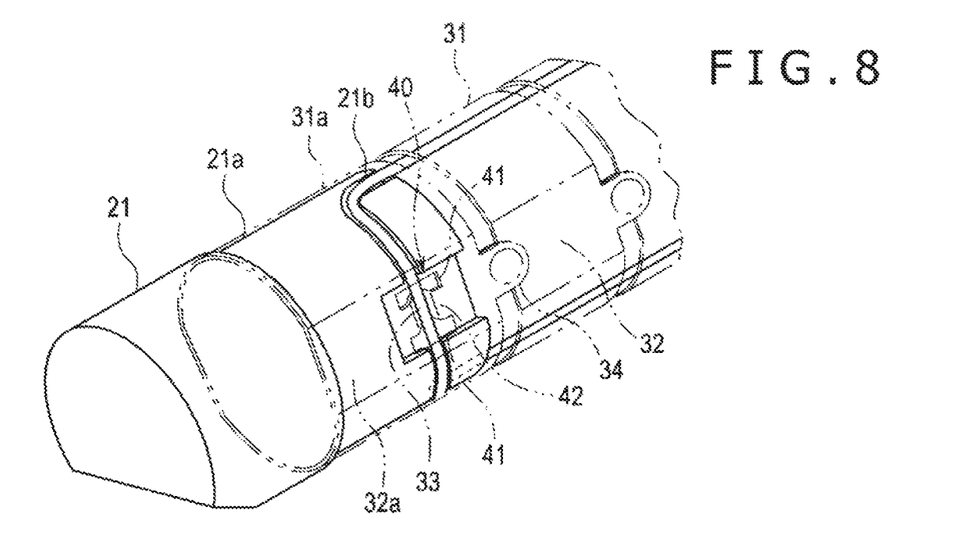
FIG. 8 is a perspective view depicting another example of a bendable tube with a distal-end rigid part fitted therein.
Figure 9:
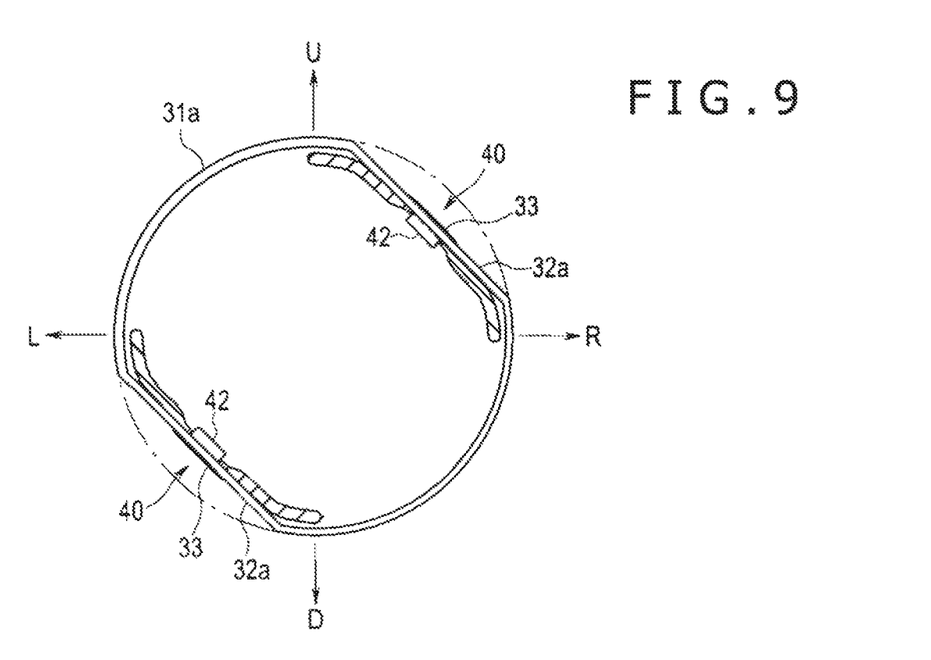

According to another example, as depicted in FIG. 8, the reduced-diameter portion 21a may have a groove 21b defined therein that accommodates the web 42 of the attaching portion 40. The bending operation wire 33 extends in the vertical directions (UD) in the reduced-diameter portion 21a. The groove 21b defines the direction in which the bending operation wire 33 extends rearwardly from the distal-end rigid part 21 to the manipulator 3 along the outer periphery of the distal-end rigid part 21, when the distal-end rigid part 21 is fitted in the distal-end bending piece 31a. Furthermore, as depicted in FIG. 9, the two flat portions 32a of the distal-end bending piece 31a may be formed at positions that are rotatably displaced 45° about the central axis "X", and may have respective attaching portions 40 by which respective bending operation wires 33 are attached, so that the bendable part 7 is of a quad-directionally bendable structure that is bendable in upward, downward, leftward, and rightward directions (UD/RL).

As described hereinbefore, the endoscope 1 according to the present embodiment allows the bending operation wire 33 to be attached to the distal-end bending piece 31a without an increase in the profile and diameter, because of the attaching portion 40 on the flat portion 32a of the distal-end bending piece 31a provided as a bending operation wire attaching structure. Consequently, the endoscope 1 makes it possible to attach the bending operation wire 33 for bending the bendable part 7 simply in position and also to prevent the insertion portion 2, particularly the bendable part 7, from increasing in the diameter.

Figure 10:
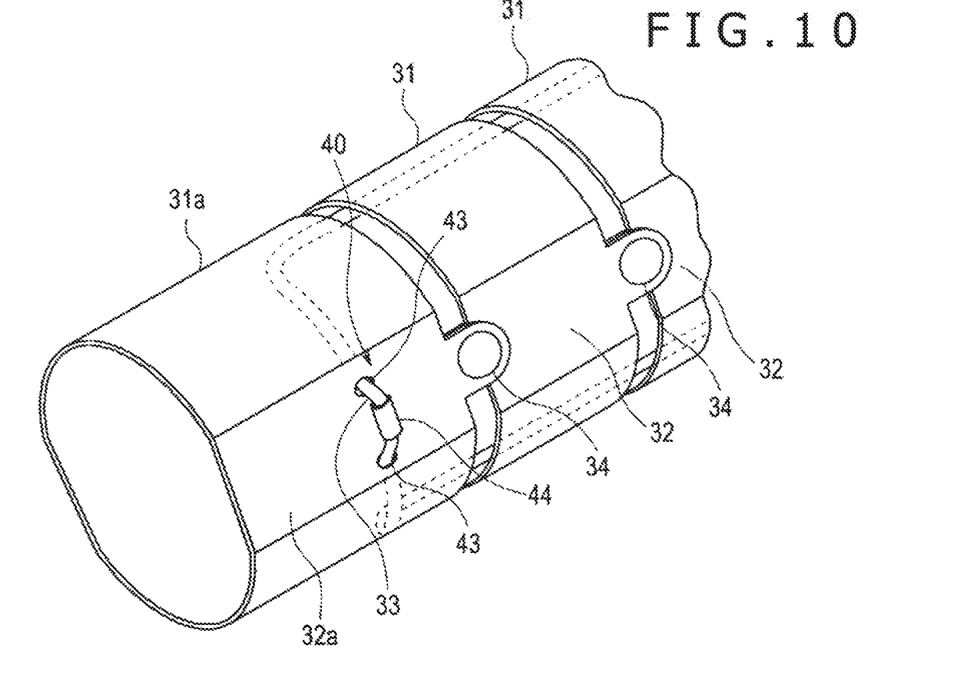
FIG. 10 is a perspective view of a distal-end bending piece with a bending operation wire attached thereto according to a first modification.
Figure 11:
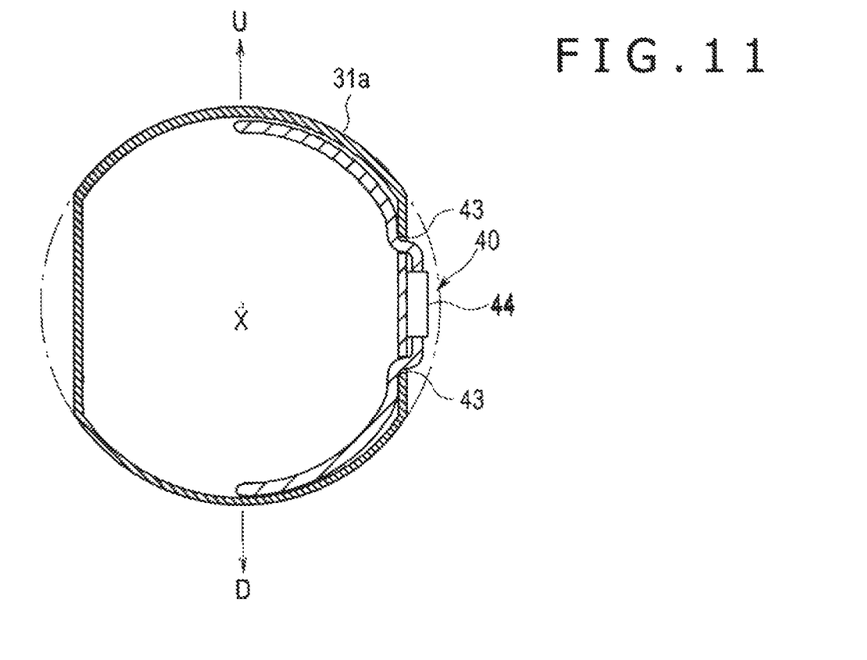
FIG. 11 is a cross-sectional view of the distal-end bending piece with the bending operation wire attached thereto according to the first modification.

A first modification of the bending operation wire attaching structure on the bendable tube 30 will be described hereinafter. FIG. 10 is a perspective view of a distal-end bending piece with a bending operation wire attached thereto according to the first modification, and FIG. 11 is a cross-sectional view of the distal-end bending piece with the bending operation wire attached thereto according to the first modification.

As depicted in FIG. 10, the attaching portion 40 has two openings 43 formed in one of the flat portions 32a of the distal-end bending piece 31a. The two openings 32 are used as wire insertion regions where the bending operation wire 33 extends from within the distal-end bending piece 31a outwardly of the distal-end bending piece 31a through one of the openings 43 and then from outside the distal-end bending piece 31a through the other opening 43 into the distal-end bending piece 31a. Between the two openings 43, a pipe 44 of metal or the like is fitted over the bending operation wire 33 that is positioned outside the distal-end bending piece 31a. The pipe 44 is crimped so that the bending operation wire 33 will not be displaced. The bending operation wire 33 is thus attached to the distal-end bending piece 31a against movement because (i) the bending operation wire 33 extends outwardly from within the distal-end bending piece 31a and inwardly from outside the distal-end bending piece 31a through the two openings 43 and (ii) the pipe 44 is crimped. Other structural details remain the same as those described hereinbefore and will not be repeated again to avoid redundancy.

The bending operation wire 33 may be attached in position (i) by attaching the pipe 44 fitted over the bending operation wire 33 to the distal-end bending piece 31a between the two openings 43 by solder or silver solder or (ii) by bonding the pipe 44 to the distal-end bending piece 31a by adhesive, rather than by crimping the pipe 44, or may be attached in position by twisting or flattening itself so that the bending operation wire 33 will be blocked against movement by the two openings 43. The endoscope 1 which incorporates the above bending operation wire attaching structure offers the same advantages as those described hereinbefore, and is of a simpler structure because only two openings 43 through which the bending operation wire 33 is inserted may be defined in one of the flat portions 32a of the distal-end bending piece 31a.

A second modification of the bending operation wire attaching structure on the bendable tube 30 will be described hereinafter.

Figure 12:
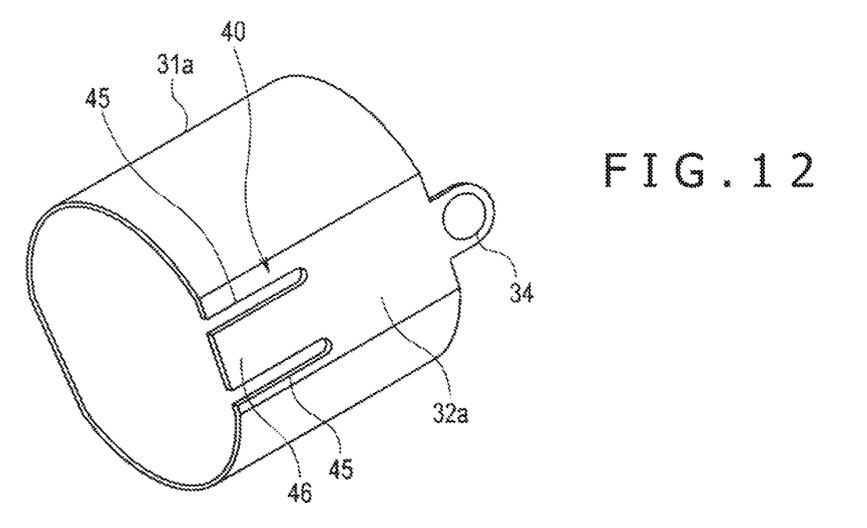
FIG. 12 is a perspective view of a distal-end bending piece according to a second modification.
Figure 13:
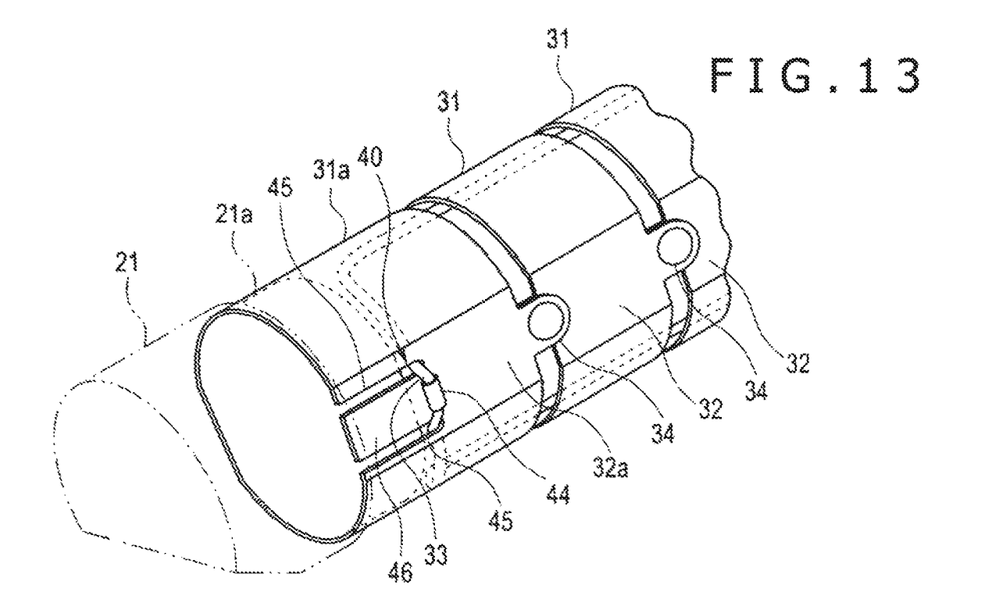
FIG. 13 is a perspective view of a bendable tube with a distal-end rigid part fitted therein according to the second modification.

FIG. 12 is a perspective view of a distal-end bending piece according to the second modification, and FIG. 13 is a perspective view of a bendable tube with a distal-end rigid part fitted therein according to the second modification. As depicted in FIG. 12, the attaching portion 40 has two slits 45 formed parallel to each other along the central axis "X" in one of the flat portions 32a of the distal-end bending piece 31a. The two slits 45 are formed as grooves and used as wire insertion regions where the bending operation wire 33 extends from within the distal-end bending piece 31a outwardly of the distal-end bending piece 31a through one of the slits 45 and then from outside the distal-end bending piece 31a through the other slit 45 into the distal-end bending piece 31a.

As depicted in FIG. 13, on the web 46 between the two slits 45, the pipe 44 of metal or the like described in the first modification is fitted over the bending operation wire 33 that is positioned outside the distal-end bending piece 31a. The pipe 44 is crimped so that the bending operation wire 33 will not be displaced, as is the case with the first modification. The bending operation wire 33 may be attached in position (i) by attaching the pipe 44 fitted over the bending operation wire 33 to the web 46 between the two slits 45 by solder or silver solder or (ii) by bonding the pipe 44 to the web 46 by adhesive, rather than by crimping the pipe 44, or may be attached in position by twisting or flattening itself so that the bending operation wire 33 will be blocked against movement by the two slits 45. The bending operation wire 33 is thus attached to the distal-end bending piece 31a against movement because (i) the bending operation wire 33 extends outwardly from within the distal-end bending piece 31a and inwardly from outside the distal-end bending piece 31a through the two slits 45 and (ii) the pipe 44 is crimped on the web 46. Other structural details remain the same as those described hereinbefore.

When the reduced-diameter portion 21a of the distal-end rigid part 21 is fitted in the distal-end bending piece 31a, the web 46 between the two slits 45 in the distal-end bending piece 31a is prevented from being deformed in a manner to collapse inwardly as the web 46 has its inner surface abutting against the reduced-diameter portion 21a. The endoscope 1 which incorporates the above bending operation wire attaching structure offers the same advantages as those described hereinbefore, and is of such a structure that it is not necessary to thread the bending operation wire 33 through the small openings 43, but it is possible to install the bending operation wire 33 simply by placing the bending operation wire 33 into the two slits 45 from the distal end of the distal-end bending piece 31a, compared with the structure of the first modification.

A third modification of the bending operation wire attaching structure on the bendable tube 30 will be described hereinafter.

Figure 14:
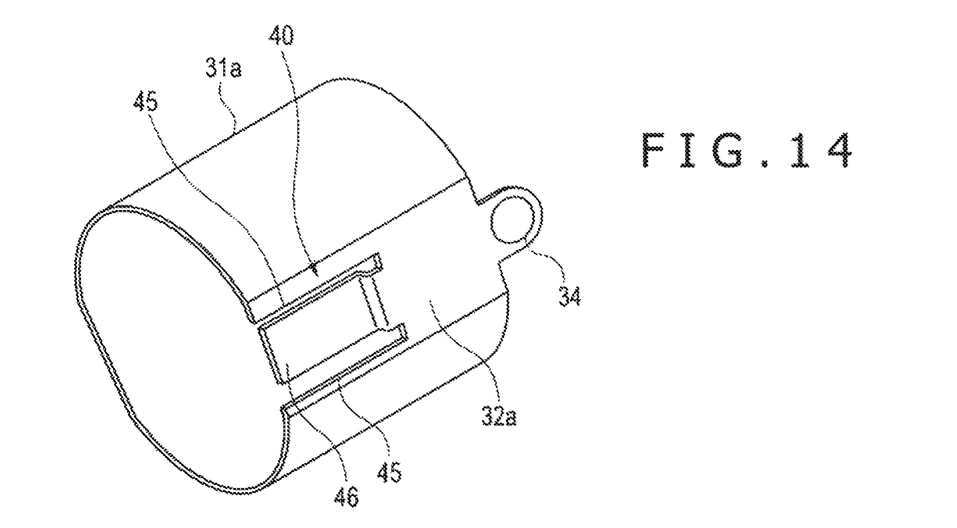
FIG. 14 is a perspective view of a distal-end bending piece according to a third modification.
Figure 15:
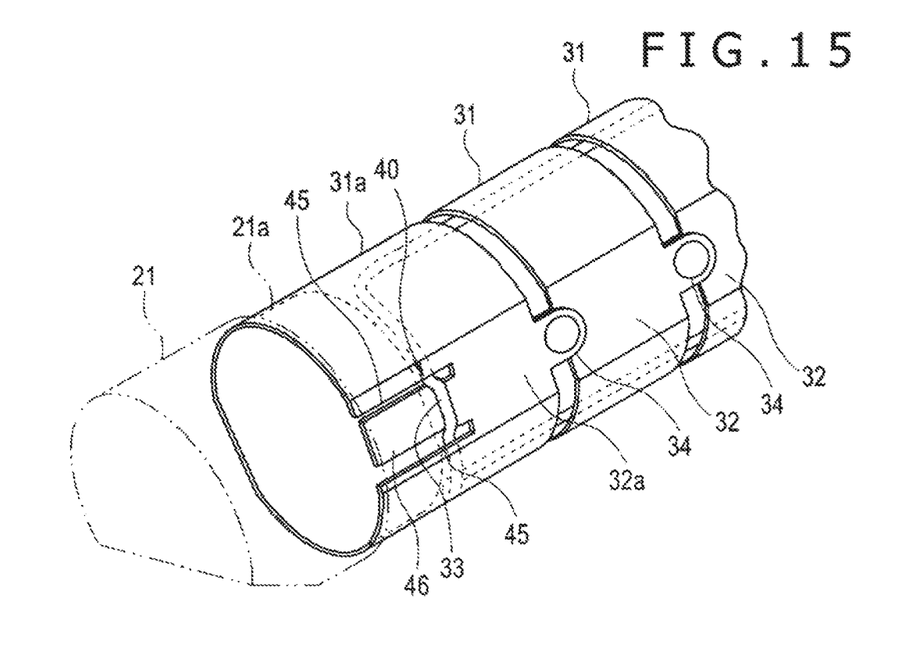
FIG. 15 is a perspective view of a bendable tube with a distal-end rigid part fitted therein according to the third modification.
Figure 16:
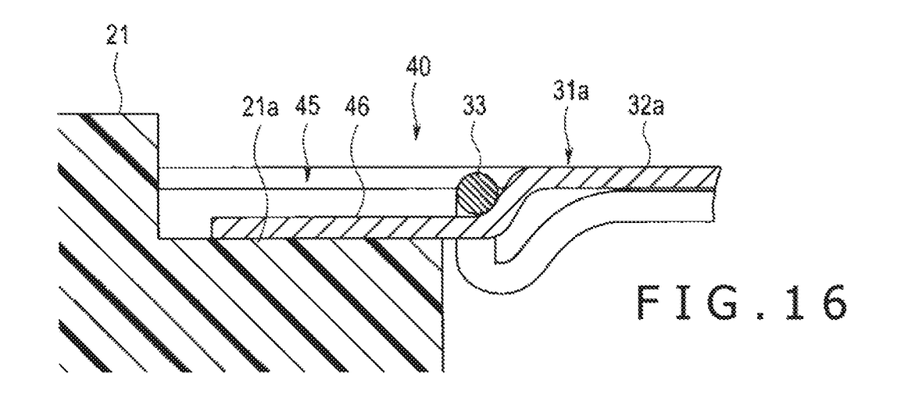
FIG. 16 is a fragmentary cross-sectional view of the distal-end bending piece with the distal-end rigid part fitted therein according to the third modification.
Figure 17:
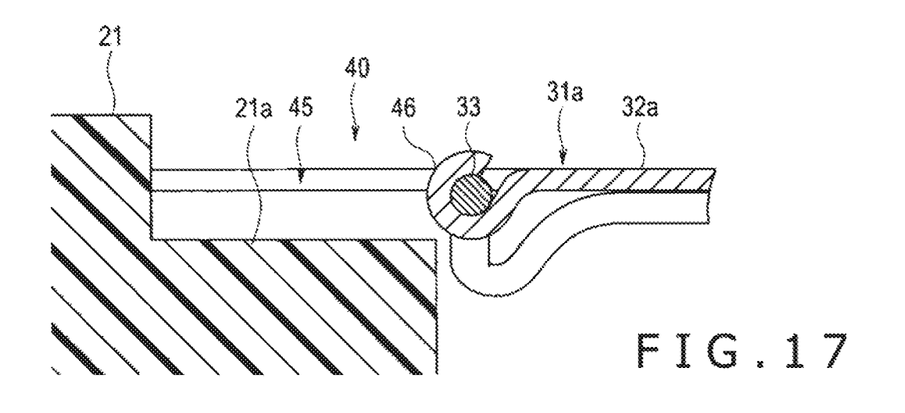
FIG. 17 is a fragmentary cross-sectional view of a distal-end bending piece with a distal-end rigid part fitted therein according to another aspect of the third modification.

FIG. 14 is a perspective view of a distal-end bending piece according to the third modification, FIG. 15 is a perspective view of a bendable tube with a distal-end rigid part fitted therein according to the third modification, FIG. 16 is a fragmentary cross-sectional view of the distal-end bending piece with the distal-end rigid part fitted therein according to the third modification, and FIG. 17 is a fragmentary cross-sectional view of a distal-end bending piece with a distal-end rigid part fitted therein according to another aspect of the third modification.

The bending operation wire attaching structure according to the present modification is of such a structure that the web 46 of the attaching portion 40 according to the second modification is folded inwardly of the distal-end bending piece 31a into a crank-shaped cross section. When the reduced-diameter portion 21a of the distal-end rigid part 21 is fitted in the distal-end bending piece 31a, the web 46 between the two slits 45 in the distal-end bending piece 31a is also prevented from being deformed in a manner to collapse inwardly as the web 46 has its inner surface abutting against the reduced-diameter portion 21a. With the arrangement according to the present modification, furthermore, the bending operation wire 33 is sandwiched against movement between the two slits 45 and the web 46 therebetween. Needless to say, a pipe 44 may be fitted over the bending operation wire 33 and crimped on the web 46, thereby securing the bending operation wire 33 immovably to the distal-end bending piece 31a. As described hereinbefore, the bending operation wire 33 may be attached to the web 46 between the two slits 45 by solder, silver solder or adhesive, or may be attached in position by twisting or flattening itself so that it will be blocked against movement by the two slits 45.

The endoscope 1 which incorporates the above bending operation wire attaching structure offers the same advantages as those described hereinbefore, and, as depicted in FIG. 16, restrains the bending operation wire 33 from projecting outwardly from the flat portion 32a of the distal-end bending piece 31a, thereby more effectively preventing the bending operation wire 33 from increasing the outside diameter of the bendable part 7, compared with the structure of the second modification. As depicted in FIG. 17, the web 46 may be crimped around the bending operation wire 33, thereby securing the bending operation wire 33 more firmly in position.

According to the present embodiment and its modifications, the bendable tube 30 is made up of the multiple bending pieces 31 (31a). However, the present disclosure is not limited to such a structure, but is also applicable to a bendable tube made of a superelastic alloy such as Ni—Ti or the like. The disclosed technology described in the above embodiment is not limited to the embodiments and its modifications, but various changes and modifications may be made therein without departing from the scope of the disclosed technology. The above embodiment covers the disclosed technology at various stages such that various embodiments can be extracted by appropriate combinations of a plurality of components that are disclosed. For example, even if some of all the components illustrated in the embodiment are deleted, insofar as the task referred to above can be accomplished and the advantages referred to above can be achieved, an arrangement free of the deleted components may be extracted.

One aspect of the disclosed technology is directed to a bendable tube bendable by a bending operation wire that comprises a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion having a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region. The bending operation wire is attached to the distal-end bending piece by the attaching portion.

One aspect of the disclosed technology is directed to a bendable tube bendable by a bending operation wire that comprises a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion having a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region being attached to the distal-end bending piece by the attaching portion.

The attaching portion includes a web disposed between the first insertion region and the second insertion region. The web is crimped outwardly of the distal-end bending piece to secure the bending operation wire in place on the web. The attaching portion has a pipe fitted over the bending operation wire between the first insertion region and the second insertion region. The pipe is crimped to secure the bending operation wire in position on the flat portion. The first insertion region and the second insertion region include openings defined in the flat portion. The first insertion region and the second insertion region include grooves defined in the flat portion and extending from a distal end of the distal-end bending piece. The attaching portion has a web disposed between the first insertion region and the second insertion region. The first insertion region and the second insertion region include grooves. The distal-end bending piece fits a fitting member for preventing the web between the grooves from being deformed inwardly. The flat portion provides a flat surface substantially parallel to a trajectory followed by a bendable part incorporating the bendable tube therein when the bendable part is bent.

Another aspect of the disclosed technology is directed to an endoscope comprises a bendable tube bendable by a bending operation wire having a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion includes a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region. The bending operation wire is attached to the distal-end bending piece by the attaching portion. An insertion portion includes the bendable tube. The insertion portion is formed as a slender tube. A manipulator joined to the insertion portion for manipulating the bendable tube. The bending operation wire is folded back and disposed in the distal-end bending piece.

Another aspect of the disclosed technology is directed to an endoscope comprises a bendable tube bendable by a bending operation wire having a plurality of bending pieces configured to be joined together. The bending pieces including a distal-end bending piece disposed at a foremost end of the bendable tube. The distal-end bending piece includes a flat portion forming a flat surface. An attaching portion is disposed on the flat portion. The attaching portion includes a first insertion region and a second insertion region. The bending operation wire is inserted from within the distal-end bending piece outwardly of the distal-end bending piece through the first insertion region. The bending operation wire is inserted from outside the distal-end bending piece into the distal-end bending piece through the second insertion region. The bending operation wire is disposed outside the distal-end bending piece between the first insertion region and the second insertion region being attached to the distal-end bending piece by the attaching portion. An insertion portion includes the bendable tube. The insertion portion is formed as a slender tube. A manipulator joined to the insertion portion for manipulating the bendable tube. The bending operation wire is folded back and disposed in the distal-end bending piece.

According to the present disclosure, there are realized a bending operation wire attaching structure and an endoscope in which a bending operation wire for bending a bendable part is attached in place in a simplified fashion and the diameter of the bendable part is prevented from increasing.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A bendable tube configured to bend using a bending operation wire, the bendable tube comprising:
   a plurality of bending pieces configured to be joined together, the bending pieces including a distal-end bending piece disposed at a distal-most end of the bendable tube, wherein:
      the distal-end bending piece includes a flat portion that includes a flat surface, and an attaching portion disposed on the flat portion,
      the attaching portion includes a first insertion region and a second insertion region,
      the first insertion region is configured to receive the bending operation wire from inside the distal-end bending piece,
      the second insertion region is configured to receive the bending operation wire from an outside surface of the distal-end bending piece, and
      the attaching portion is configured to be attached to a portion of the bending operation wire disposed outside the distal-end bending piece between the first insertion region and the second insertion region.

2. The bendable tube of claim 1, wherein the attaching portion includes a web disposed between the first insertion region and the second insertion region, and the web is crimped outwardly of the distal-end bending piece to secure the bending operation wire in place on the web.

3. The bendable tube of claim 1, wherein the attaching portion has a pipe fitted over the bending operation wire between the first insertion region and the second insertion region, and the pipe is crimped to secure the bending operation wire in position on the flat portion.

4. The bendable tube of claim 1, wherein the first insertion region and the second insertion region include openings defined in the flat portion.

5. The bendable tube of claim 1, wherein the first insertion region and the second insertion region include grooves defined in the flat portion and extending from a distal end of the distal-end bending piece.

6. The bendable tube of claim 1, wherein the attaching portion has a web disposed between the first insertion region and the second insertion region, and the first insertion region and the second insertion region include grooves, and wherein the distal-end bending piece fits a fitting member for preventing the web between the grooves from being deformed inwardly.

7. The bendable tube of claim 1, wherein the flat surface of the flat portion is parallel to a path a bendable part of the bending operation wire is configured to follow.

8. The bendable tube of claim 1, wherein when the bending operation wire is inserted into the distal end bending piece, the bending operation wire is folded.

9. An endoscope comprising:
   a bendable tube configured to bend using a bending operation wire, the bendable tube including:
      a plurality of bending pieces configured to be joined together, the bending pieces including a distal-end bending piece disposed at a distal-most end of the bendable tube, the distal-end bending piece including:
         a flat portion that includes a flat surface, and
         an attaching portion disposed on the flat portion, the attaching portion including a first insertion region and a second insertion region, wherein:
            the first insertion region is configured to receive the bending operation wire from inside the distal-end bending piece outwardly of the distal-end bending piece;
            the second insertion region is configured to receive the bending operation wire from outside the distal-end bending piece such that when the bending operation wire is provided in the bendable tube, a portion of the bending operation wire disposed outside the distal-end bending piece between the first insertion region and the second insertion region is configured to be attached to the distal-end bending piece via the attaching portion;
   an insertion portion including the bendable tube, the insertion portion being a tube; and
   a manipulator attached to the insertion portion to manipulate the bendable tube.

* * * * *